United States Patent
Horsman et al.

(10) Patent No.: US 6,629,626 B1
(45) Date of Patent: Oct. 7, 2003

(54) LIQUID TRANSFER DEVICE

(75) Inventors: Jeffrey A. Horsman, Charlottesville, VA (US); Ivan Hargro, Syracuse, NY (US); Peter Rahn, Palmyna, VA (US)

(73) Assignee: Dyax, Corporation, Cambridge, MA (US)

( * ) Notice: Subject to any disclaimer, the term of this patent is extended or adjusted under 35 U.S.C. 154(b) by 0 days.

(21) Appl. No.: 09/519,784

(22) Filed: Mar. 7, 2000

(51) Int. Cl.$^7$ .................................................. B01L 3/02
(52) U.S. Cl. ................. 222/420; 73/864.72; 73/863.31; 436/180; 422/100
(58) Field of Search ............................. 222/420, 421, 222/422; 73/864.72, 863.31, 863.32; 436/180; 422/100, 930

(56) References Cited

U.S. PATENT DOCUMENTS

| | | | | |
|---|---|---|---|---|
| 2,396,470 A | * | 3/1946 | Mortensen | 73/864.01 X |
| 2,595,493 A | * | 5/1952 | Slaby et al. | 73/864.11 |
| 3,222,942 A | * | 12/1965 | Davis et al. | 74/102 |
| 3,644,933 A | * | 2/1972 | Tullos et al. | 346/140.1 |
| 4,260,467 A | * | 4/1981 | Smith et al. | 204/413 |
| 4,334,879 A | | 6/1982 | Fujimori | 23/230 R |
| 4,478,094 A | * | 10/1984 | Salomaa et al. | 73/863.32 |
| 5,208,163 A | * | 5/1993 | Charlton et al. | 436/180 X |
| 5,578,178 A | * | 11/1996 | Nuzzio | 204/413 |
| 6,024,925 A | | 2/2000 | Little et al. | 422/100 |
| 6,196,671 B1 | * | 3/2001 | Breemes, Sr. et al. | 347/86 |
| 6,269,846 B1 | * | 8/2001 | Overbeck et al. | 422/100 X |

FOREIGN PATENT DOCUMENTS

| | | | | |
|---|---|---|---|---|
| JP | 10-128129 | | 5/1998 | B01L/3/02 |
| WO | WO 98/20020 | * | 5/1998 | B01J/19/00 |
| WO | WO 99/05308 | | 2/1999 | B01L/3/02 |
| WO | WO 99/36760 | | 7/1999 | G01N/1/14 |

OTHER PUBLICATIONS

Derwent–ACC–No: 1980–19893C abstract of SU 672495 A Kalugin et al "External controlled dispenser for droplet analysis –with accuracy increased by spring–loading of capillary having electromagnetic drive, for small quantity dispensing", Jul. 1979.*

International Search Report for PCT/US01/07267 (for WO 200166251 A3 no publication date, WO 200166251 A2 published Sep. 13, 2001, search report mailed to Applicant Oct. 9, 2001).

* cited by examiner

Primary Examiner—Thomas P. Noland
(74) Attorney, Agent, or Firm—Fish & Richardson P.C.

(57) ABSTRACT

A device for transferring small drops of liquid from one or more liquid holders to one or more liquid destinations is disclosed. The device includes a support member and a plurality of fluid transfer members extending from the support member. Each fluid transfer member includes a flexible liquid transfer end.

6 Claims, 14 Drawing Sheets

LIQUID TRANSFER DEVICE

BACKGROUND OF THE INVENTION

The invention relates to devices for transferring small amounts of liquid from a liquid holder to a liquid destination, e.g., a thin layer chromatography plate.

Thin layer chromatography is a technique for analyzing the components of a liquid sample. In thin layer chromatography, a flat plate is covered with an absorbent media, or a "stationary phase." A drop of sample dissolved in a solvent, or a "mobile phase," is applied to the flat plate. Due to capillary action, the solvent moves along the absorbent media on the plate. As the solvent moves, the components of the sample separate and deposit on the absorbent media at different points, depending on certain characteristics of the component, such as molecular weight and affinity for the absorbent media. Once the solvent has stopped traveling and has completed depositing the components of the sample, a technician can analyze the patterns and materials deposited on the plate to determine information about the composition of the sample.

To begin thin layer chromatographic analysis, a technician must transfer a drop of the sample-solvent mixture from a liquid holder, e.g., a test tube, to the flat plate. Typically, a laboratory technician transfers small amounts of liquid using a thin, rigid glass or plastic tube called a pipette. To transfer liquid with a pipette, an end of the pipette is placed in contact with liquid in the test tube. Since the diameter of the pipette is small, a drop of liquid is drawn into the tube by capillary action. The tube, with the drop inside, is then transferred to the flat plate. When the open end of the tube is touched against the absorbent media on the glass plate, capillary action pulls the drop of liquid from the pipette to the absorbent media.

Conventional pipettes, however, have certain limitations. Since pipettes are typically rigid and fragile, pressing a pipette against a flat surface with too much force can break the pipette. For this reason, technicians generally must transfer liquid from test tubes to a thin layer chromatography plate one pipette at a time, and one drop at a time.

SUMMARY OF THE INVENTION

In one aspect, the invention features a device for transferring small drops of liquid from one or more liquid holders to one or more liquid destinations. The device includes a support member and a plurality of fluid transfer members extending from the support member. Each fluid transfer member includes a flexible liquid transfer end.

Embodiments of this aspect of the invention may include one or more of the following features.

The fluid transfer members have a generally elongated shape, and extend from the support member axially in a parallel arrangement. Each transfer member is sized and shaped to fit within a test tube.

The device further includes an adjusting mechanism, e.g., a spring, that allows a user to vary the distance between two fluid transfer members. For example, the device can include separate adjusting mechanisms connecting each fluid transfer member to adjacent fluid transfer members, such that a user can simultaneously vary the distance between all the fluid transfer members.

The fluid transfer ends can include a sponge tip. For example, the fluid transfer end can be a rigid shaft that includes a sponge tip, the shaft being removably attached to a holder. The device can further include a plunger that, when activated, ejects one or more fluid transfer ends from its holder.

The sponge tips are made from urea formaldehyde, polyethylene, or cotton, and have diameters less than about 1.5 mm.

Instead of a sponge tip, each fluid transfer end can include a capillary tube at its distal tip and an axially extending spring. The spring is coupled to, e.g., a proximal end of the capillary tube such that the spring provides axial flexibility to the tube.

In the capillary tube embodiment, each fluid transfer member can include a rigid sleeve and a pin. The sleeve has a proximal region that surrounds the spring and a distal region that defines the capillary tube, and the pin has a shaft and a head. The shaft of the pin extends axially into the spring, and the head of the pin is coupled to a holder. Each holder defines a threaded bore and includes a pair of screws threadingly engaged with the bore. The head of the pin is disposed within the bore between the two screws. The capillary tube also defines a transverse hole to prevent air from becoming trapped within the tube.

In another aspect, the invention features a fluid transfer tool for use with the fluid transfer devices described herein. The tool includes an axially extending spring, a capillary tube coupled to a distal end of the spring, and a pin. The pin has a shaft disposed within the interior of spring, and a head that remains proximal to the proximal end of the spring. The tool also includes an attachment mechanism, such as a threaded screw, for coupling the tool to the fluid transfer device. The tool can be, e.g., a replacement fluid transfer end for the fluid transfer device, and can be sold separately from the device.

In another aspect, the invention features a method of transferring a drop of liquid from a liquid holder to a liquid destination (e.g., a thin layer chromatography plate or an electrophoresis gel). The method includes: (a) providing a fluid transfer device that has an elongated shaft with a flexible, liquid transfer end; (b) contacting the end with liquid in the liquid holder, such that the end collects a drop of liquid; and (c) contacting the end against the liquid destination, such that the tip releases the drop of liquid.

Embodiments of this aspect of the invention may include one or more of the following features.

The drop of liquid is less than about 0.005 ml in volume. The liquid transfer end includes a sponge tip, or is spring mounted, the spring providing the end with axial flexibility.

In another aspect, the invention features a method of simultaneously transferring a plurality of liquid drops from one or more liquid holders to one or more liquid destinations. The method includes: (a) providing a fluid transfer device that has a support member and a plurality of fluid transfer members extending from the support member, where each fluid transfer member includes a flexible, liquid transfer end; (b) contacting the liquid transfer end of more than one fluid transfer member with liquid in one or more liquid holders, such that each end contacted with liquid collects a drop of liquid; and (c) simultaneously contacting the liquid absorbing end of each more than one fluid transfer members against one or more liquid destinations, such that each end contacted with a liquid destination releases its collected drop to the liquid destination.

Embodiments of this aspect of the invention may include one or more of the following features. The fluid transfer members extend axially from the support member, and each liquid transfer end is axially flexible. For example, each fluid transfer end includes a capillary tube at its distal tip, and an axially extending spring, the spring being coupled to the capillary tube such that the spring provides the axial flexibility to the tube. The second contacting step includes pressing the distal tip of at least one fluid transfer end against a surface of the liquid destination, such that the spring of the at least one fluid transfer member is compressed. Alternatively, the liquid transfer ends can each include a sponge tip.

The first contacting step includes contacting each end in the device with liquid in a liquid holder, and the second contacting step includes contacting each end in the device against a liquid destination.

The liquid destination is, e.g., a thin layer chromatography plate, and the one or more liquid holders is an array of test tubes. The first contacting step includes simultaneously contacting different liquid absorbing tips with liquid in different test tubes.

Each fluid transfer member can have a disposable portion that includes its liquid transfer end. If the ends are disposable, the method further includes removing one or more disposable portions from the device after contacting one or more ends against a liquid destination.

Embodiments of the invention may include one or more of the following advantages. The flexible fluid transfer ends are less likely to break when pressed against, e.g., a thin layer chromatography plate. The flexibility of the ends allows the device to tolerate some variation in the lengths of the fluid transfer members.

The fluid transfer devices are safer to use than rigid pipettes, since the fluid transfer ends are less likely to break than pipettes, and therefore less likely to expose a user to chemicals.

Since the fluid transfer devices can transfer liquid from multiple liquid holders to multiple liquid destinations simultaneously, they are faster to use than individual pipettes.

DESCRIPTION OF THE PREFERRED EMBODIMENT

Embodiments of the invention include fluid transfer devices that allow simultaneously transfer of multiple drops of liquid from a liquid source (e.g., a row of test tubes) to a liquid destination (e.g., a thin layer chromatography plate). The devices include a plurality of fluid transfer members extending from a support member. Each fluid transfer member includes a flexible fluid transfer end for transferring a drop of liquid. Since the ends are flexible, they are less likely to break than conventional pipettes when pressed against a flat surface, such as a thin layer chromatography plate. As a result, the device will successfully transfer multiple drops at once, even if the fluid transfer ends are not all exactly aligned.

Figure 1:
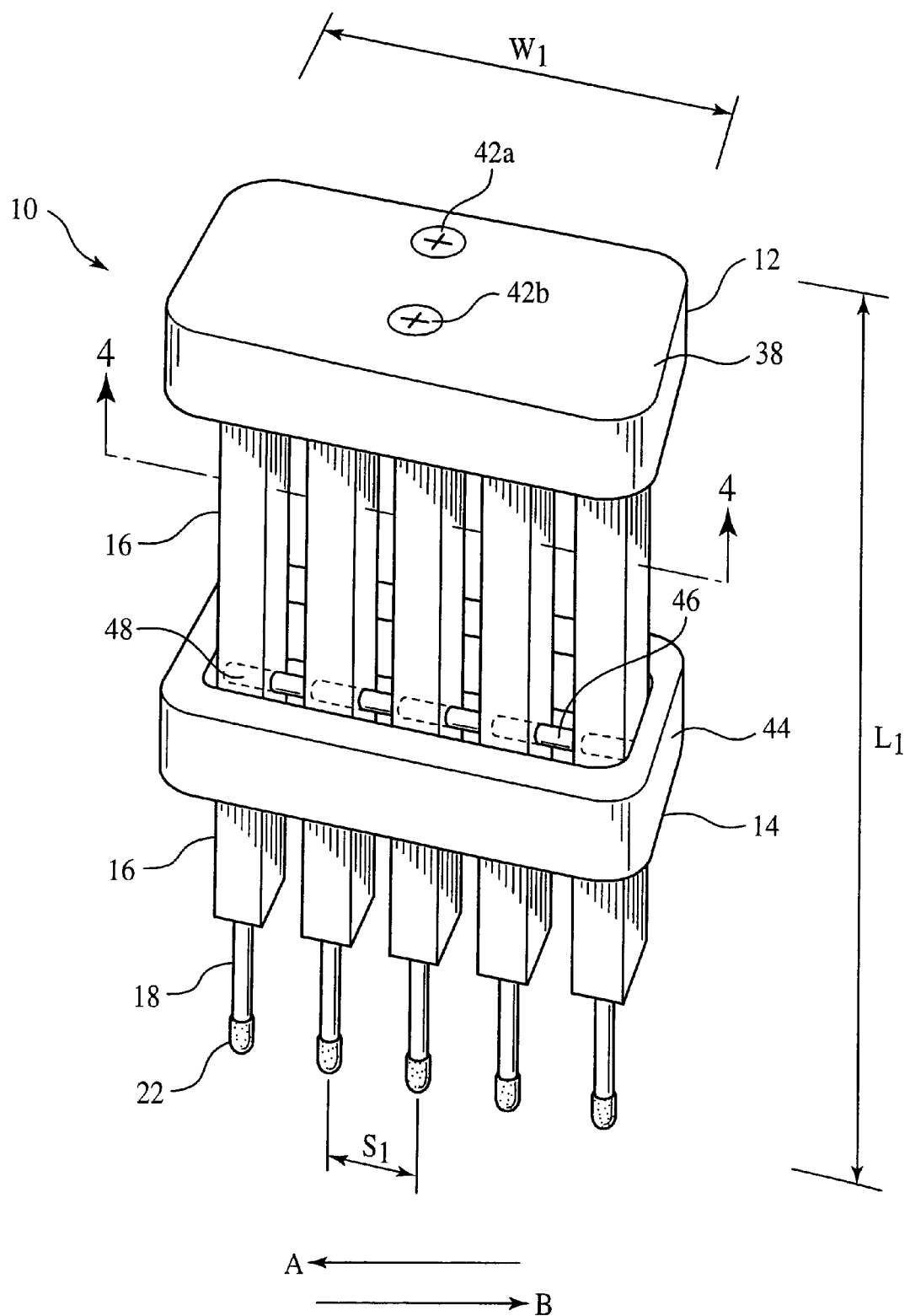
FIG. 1 is a perspective view of a fluid transfer device with its stick holders in an expanded position.
Figure 2:
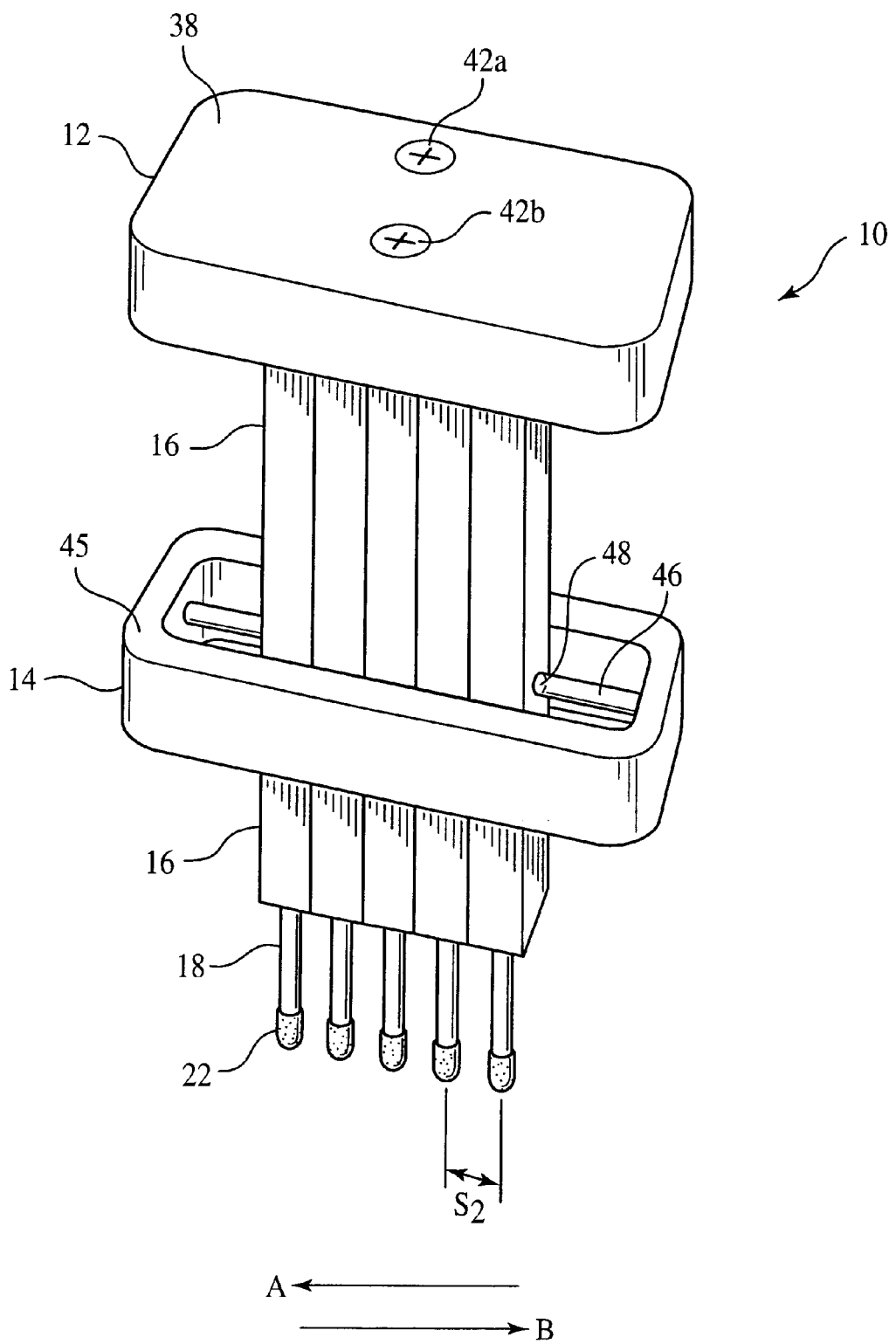
FIG. 2 is a perspective view of the fluid transfer device of FIG. 1 with its stick holders in a contracted position.

Referring to FIGS. 1 and 2, a fluid transfer device 10 includes an upper support rack 12, a lower support rack 14, five stick holders 16, and five disposable fluid transfer sticks 18. The five stick holders 16 are slidable in the directions of arrows A and B between an expanded position, as shown in FIG. 1, and a contracted position, as shown in FIG. 2. Sliding the stick holders in the direction of arrows A or B, i.e., moving the holders closer together or further apart, allows a user to vary the distance between the fluid transfer sticks 18.

Figure 3:
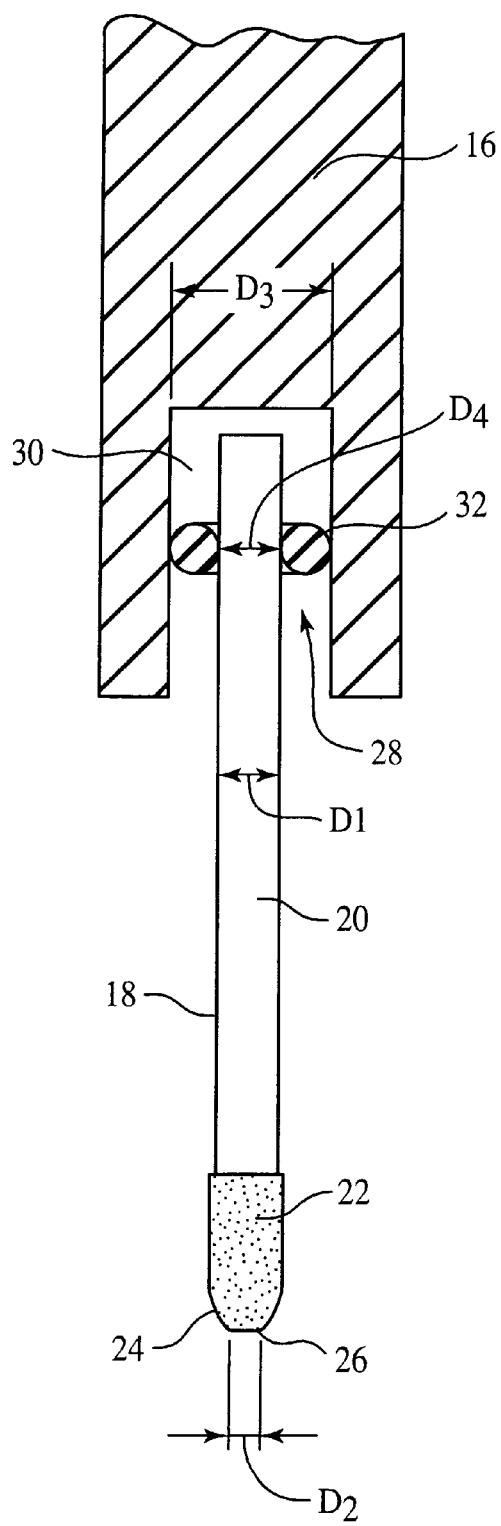
FIG. 3 is an enlarged, sectional view of a stick holder and fluid transfer stick of the device of FIG. 1.

Referring to FIG. 3, each fluid transfer stick 18 includes a shaft 20 and a sponge tip 22. The sponge tip has a tapered end 24, creating a narrow fluid transfer point 26. Shaft 20 has a diameter $D_1$, and point 26 has a diameter $D_2$ smaller than $D_1$. Sponge tip 22 is attached to shaft 20 using, e.g., a glue.

Each disposable transfer stick 18 is engaged with a stick holder 16 using an interference fit 28. Each stick holder 16 includes a bore 30 and an O-ring 32. Bore 30 has a diameter $D_3$ larger than diameter $D_1$ of shaft 20, and O-ring 32 has an inner diameter $D_4$ slightly smaller than diameter $D_1$. Stick 18, therefore, can be removably engaged with a holder 16 by inserting shaft 20 through O-ring 32.

Figure 4A:
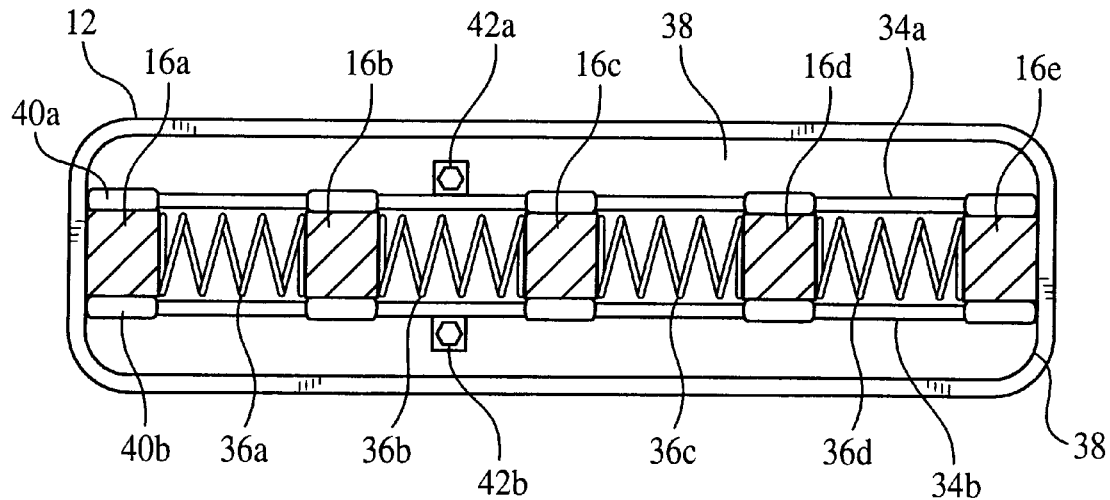
FIG. 4A is a sectional view of the device of FIG. 1, taken along the line 4—4 in FIG. 1.

FIGS. 1, 2, and 4A–4B illustrate the attachment of stick holders 16 to upper support rack 12 and lower support rack 14. Referring to FIG. 4A, upper support rack 12 includes two sliding rails 34a, 34b, four springs 36a, 36b, 36c, and 36d, and an upper housing 38. Each holder 16 is attached to rails 34a, 34b via two attachment clips 40a, 40b. Clips 40a, 40b surround rails 34a, 34b, allowing each holder 16 to be slidable in the directions of arrows A and B. Clips 40a, 40b can be, e.g., c-clips. Rails 34a, 34b are attached to upper housing 38 of upper rack 12 via bolts 42a, 42b.

Spring 36a is compressed between holder 16a and 16b, spring 36b is compressed between holder 16b and 16c, spring 36c is compressed between holder 16c and 16d, and spring 36d is compressed between holder 16d and 16e.

Springs 36a–36d bias holders 16 in their expanded position, as shown in FIGS. 1 and 4A.

Figure 4B:
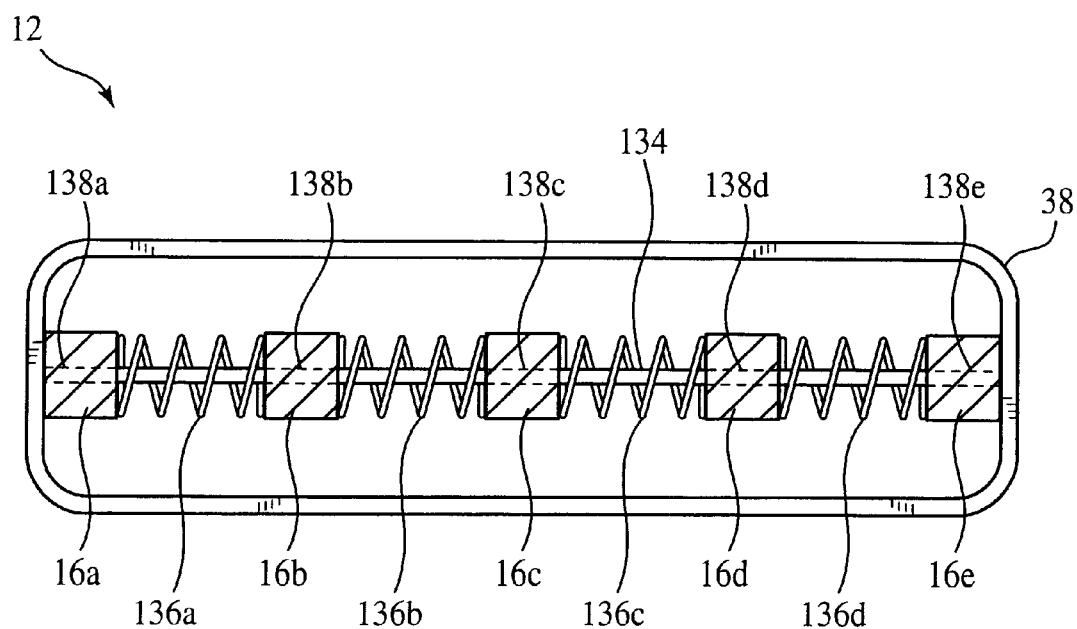
FIG. 4B is a sectional view of an alternate embodiment of an upper support rack in the device of FIG. 1, taken along the line 4—4 in FIG. 1.

Alternatively, instead of sliding rails 34a, 34b, upper rack 12 can include a transverse bar 134. Referring to FIG. 4B, bar 134 passes through a transverse hole 138 in each stick holder 16. Springs 136a, 136b, 136c, and 136d surround bar 134 and connect stick holders 16a–16d, as described with reference to FIG. 4A. Springs 136a–136d bias holders 16 in their expanded position.

Lower rack 14 includes a rectangular annular lower housing 44 and a transverse rod 46 that passes through transverse holes 48 in stick holders 16. The diameter of rod 46 is close to, but slightly less than, the diameter of each hole 48, such that rod 46 passes snugly through the holes 48. Rod 46 can include, e.g., a lubricant to facilitate sliding of holders 16. Lower rack 14 and rod 46 add additional support to holders 16, and prevent holders 16 from rotating when a user slides holders 16 from their expanded position to their contracted position. Lower rack 14 can also include springs connecting stick holders 16, as described above with reference to FIG. 4B. Rod 46 is attached to lower housing 44 using, e.g., bolts (not shown).

Upper housing 38, lower housing 44, rod 46, and holders 16 can be made from, e.g., a hard plastic, such as a polycarbonate, or a metal, such as aluminum. Rails 34a, 34b and clips 40a, 40b can be, e.g., a metal such as aluminum. Shafts 20 of disposable sticks 18 can be, e.g., wood, cardboard, polyethylene, or any other inexpensive rigid plastic. Sponge tips 22 can be, e.g., cotton, urea formaldehyde, porous polyethylene, or any other synthetic sponge material. Other types of porous, non-sponge materials can also be used, so long as the material has sufficient flexibility, and can transfer a drop of liquid.

The non-disposable components of device 10, including upper housing 38, lower housing 44, rod 46, and holders 16 can be manufactured using, e.g., injection molding. Stick 18 can be made, e.g., by molding shaft 20 and then gluing tip 22 onto an end of shaft 20. Other techniques known in the art can be used to manufacture the components of device 10.

Device 10 has an overall length $L_1$ of, e.g., about 15 cm, and an overall width $W_1$ of, e.g., about 10 cm. Diameter $D_1$ of shaft 20 is, e.g., about 5 mm. Diameter $D_2$ of tip 22 is, e.g., less than 1.5 mm, e.g., about 1 mm. Diameter $D_3$ of bore 30 is, e.g., about 12 mm, and diameter $D_4$ of O-ring 32 is, e.g., about 4.5 mm. When holders 16 are in their expanded position, as shown in FIG. 1, each tip 22 is separated from adjacent tips by a distance $S_1$ of, e.g., about 13 mm. When holders 16 are in their contracted position, as shown in FIG. 2, separation distance $S_2$ between adjacent tips is, e.g., about 7 mm.

Figure 5A:
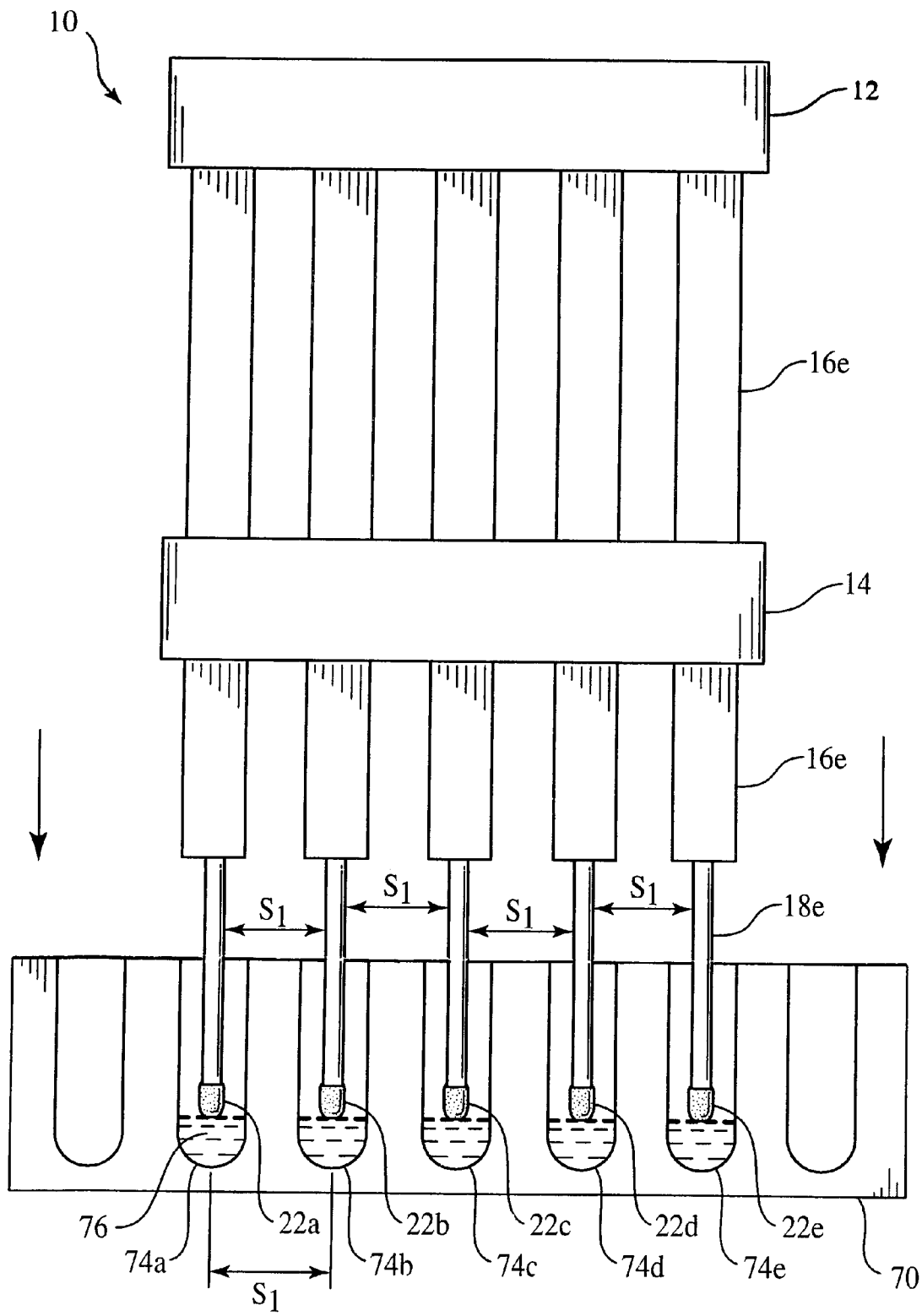
FIG. 5A is a perspective view of the device of FIG. 1 absorbing fluid from test tubes.
Figure 5B:
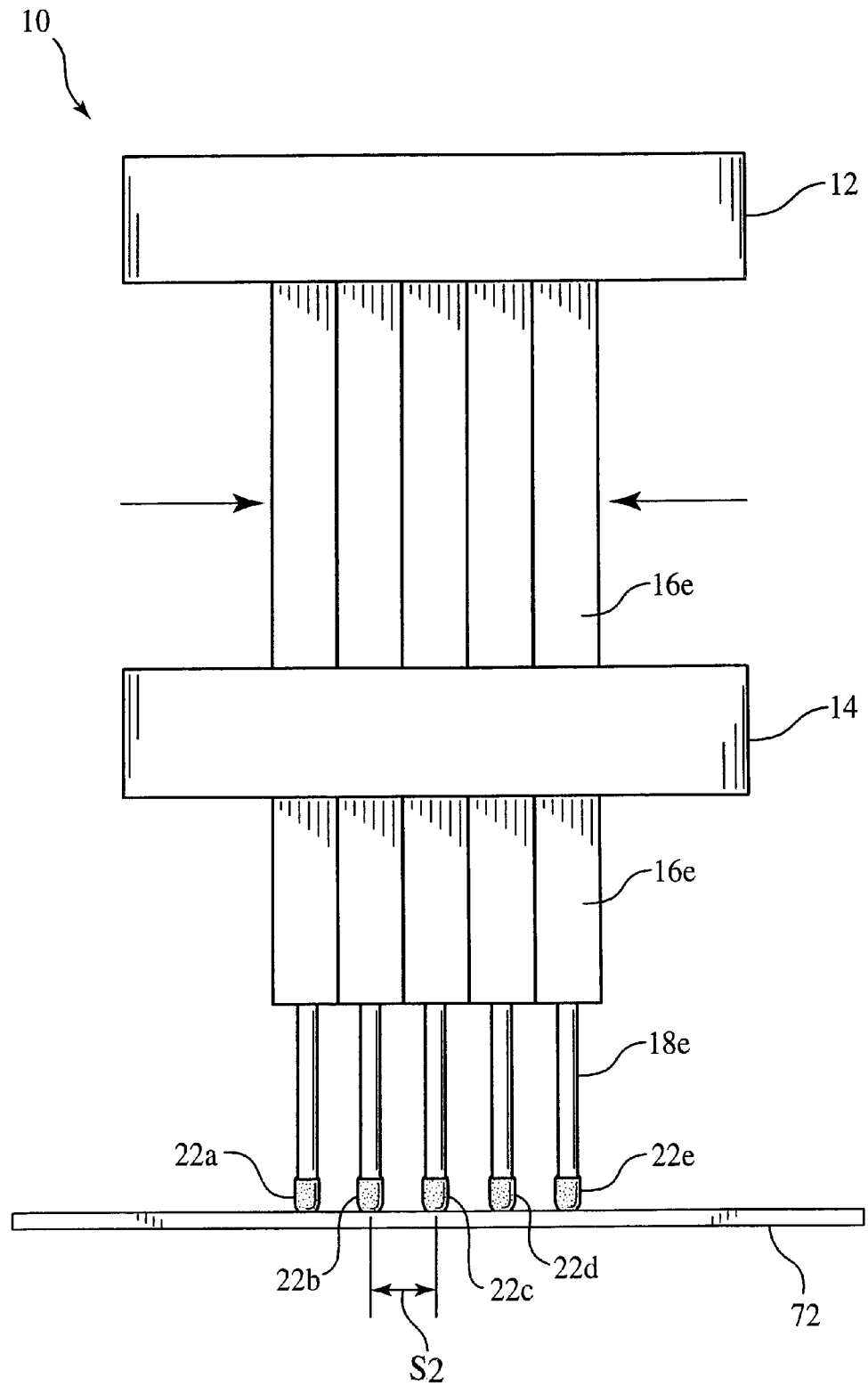
FIG. 5B is a perspective view of the device of FIG. 5A depositing absorbed fluid onto a thin layer chromatography plate.

FIGS. 5A and 5B illustrate use of device 10 to transfer liquid from a test tube array 70 to a thin layer chromatography plate 72. Referring to FIG. 5A, array 70 includes five test tubes 74a, 74b, 74c, 74d, and 74e, each tube partially filled with a liquid 76. Test tubes 74a–74e are spaced apart by separation distance $S_1$, the same distance which separates the tips 22 in device 10 when device 10 is in its default, expanded position. To transfer liquid, device 10 is first lowered into tubes 74a–74e simultaneously, as shown in FIG. 5A. Sponge tips 22a–22e absorb a small amount of liquid 76 (e.g., 0.005 ml). Device 10 is then removed from array 70.

Referring to FIG. 5B, a user then squeezes stick holders 16 together, compressing springs 36a–36d, and forcing device 10 from its expanded to its contracted position. While maintaining device 10 in its contracted position, the user presses tips 22 against thin layer chromatography plate 72. Compression of sponge tips 22 forces absorbed liquid from sponge tip 22 to the surface of plate 72, depositing five drops of liquid onto plate 22. Since tips 22 are pressed against plate 72 while device 10 is in its contracted position, the drops will be spaced apart by distance $S_1$. Device 10 can be designed so that distance $S_1$ is the ideal separation distance for thin layer chromatography, e.g., about 7 mm.

After depositing the five drops of liquid, disposable sticks 18 are removed from device 10 by pulling shafts 20 out of bores 30. The used sticks 18 are discarded, and new disposable sticks 18 are inserted into bores 30. The process can then be repeated, drawing liquid from the same test tubes 74a–74e, or from different test tubes in array 70.

Since sponge tips 22 are flexible, holders 16 and disposable sticks 18 need not all be precisely the same length for device 10 to effectively transfer liquid. If one stick 18 is slightly longer, e.g., 0.5 mm longer, the difference in height will not prevent the shorter sticks 18 from reaching plate 72 and depositing liquid. When the user presses tips 22 against plate 72, the sponge tip 22 of the longer stick will compress slightly more, allowing all tips 22 to deliver liquid. By contrast, if sticks 18 were rigid pipettes, a small difference in stick length would either prevent the shorter sticks from reaching plate 72, or would cause the longer stick to break.

Other embodiments are within the scope of the claims. For example, the sponge tips of sticks 18 can be formed or attached in a different manner. Rather than gluing a sponge tip 22 onto shaft 20, shaft 20 can have a point that pierces a sponge tip, attaching the sponge to the shaft. Alternatively, shaft 20 can be a hollow tube containing a sponge material. The sponge material can extrude from the end of the hollow shaft, forming tip 22.

Figure 6:
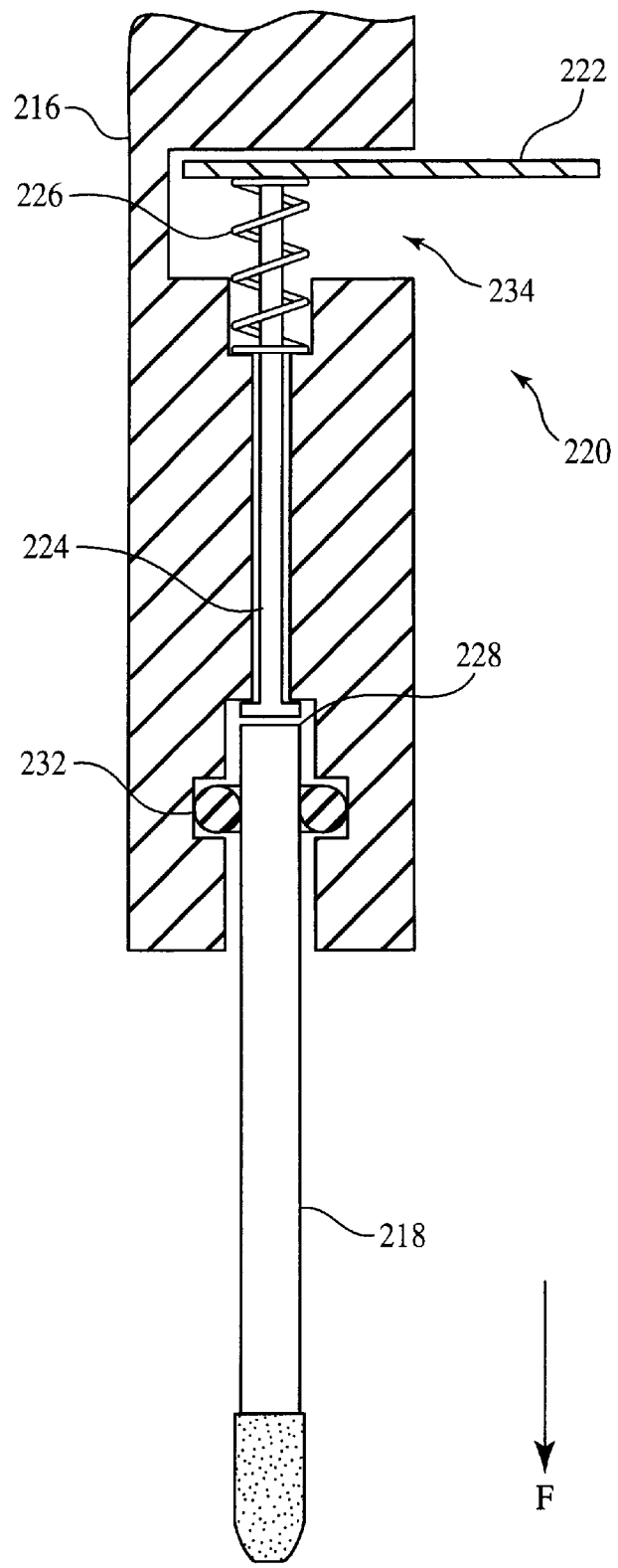
FIG. 6 is an enlarged, sectional view of an ejection system for ejecting a disposable fluid transfer stick from a stick holder.

Device 10 can include an ejector system to simplify removal of used sticks 18. Referring to FIG. 6, a holder 216 can include a ejector system 220 for ejecting a used stick 218. Ejector system 220 includes a plunger 222 attached to an ejection shaft 224, and a spring 226. Spring 226 biases ejection shaft 224 away from a proximal end 228 of stick 218. Plunger 222 extrudes from holder 216 through a slit 234 in holder 216, allowing a user to reach the plunger.

To eject stick 218, a user forces plunger 222 in the direction of arrow F, causing shaft 224 to push end 228 of stick 218 in the direction of arrow F. If the force exerted on stick 218 is sufficiently strong to overcome the interference fit of O-ring 232, then stick 218 is ejected from holder 216.

Figure 7A:
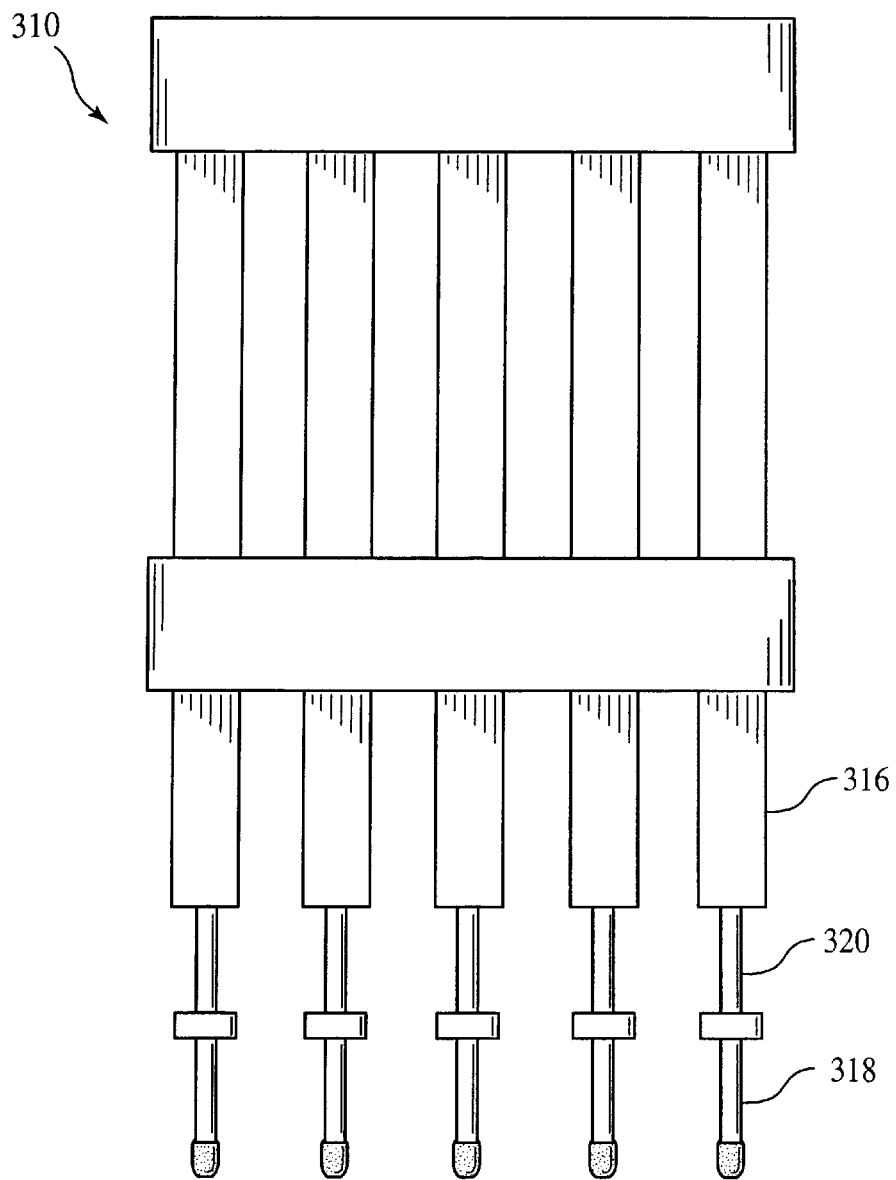
FIG. 7A is a perspective view of an alternate embodiment of the device of FIG. 1, showing fluid transfer sticks having collars.
Figure 7B:
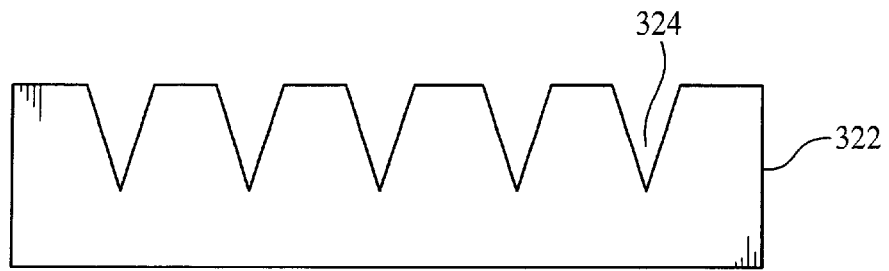
FIG. 7B is a perspective view of a grooved removal tray for removing fluid transfer sticks from the device of FIG. 7A.

Alternatively, the shafts of the disposable sticks can have collars, allowing used sticks to be removed using a grooved removal tray Referring to FIGS. 7A and 7B, each stick 318 on device 310 has a collar 320. A removal tray 322 has five pointed grooves 324. To remove sticks 318, a user holds tray 322 in place, and drags sticks 318 across grooves 324. Collars 320 catch in grooves 324, pulling sticks 318 out of holders 316.

Figure 8A:
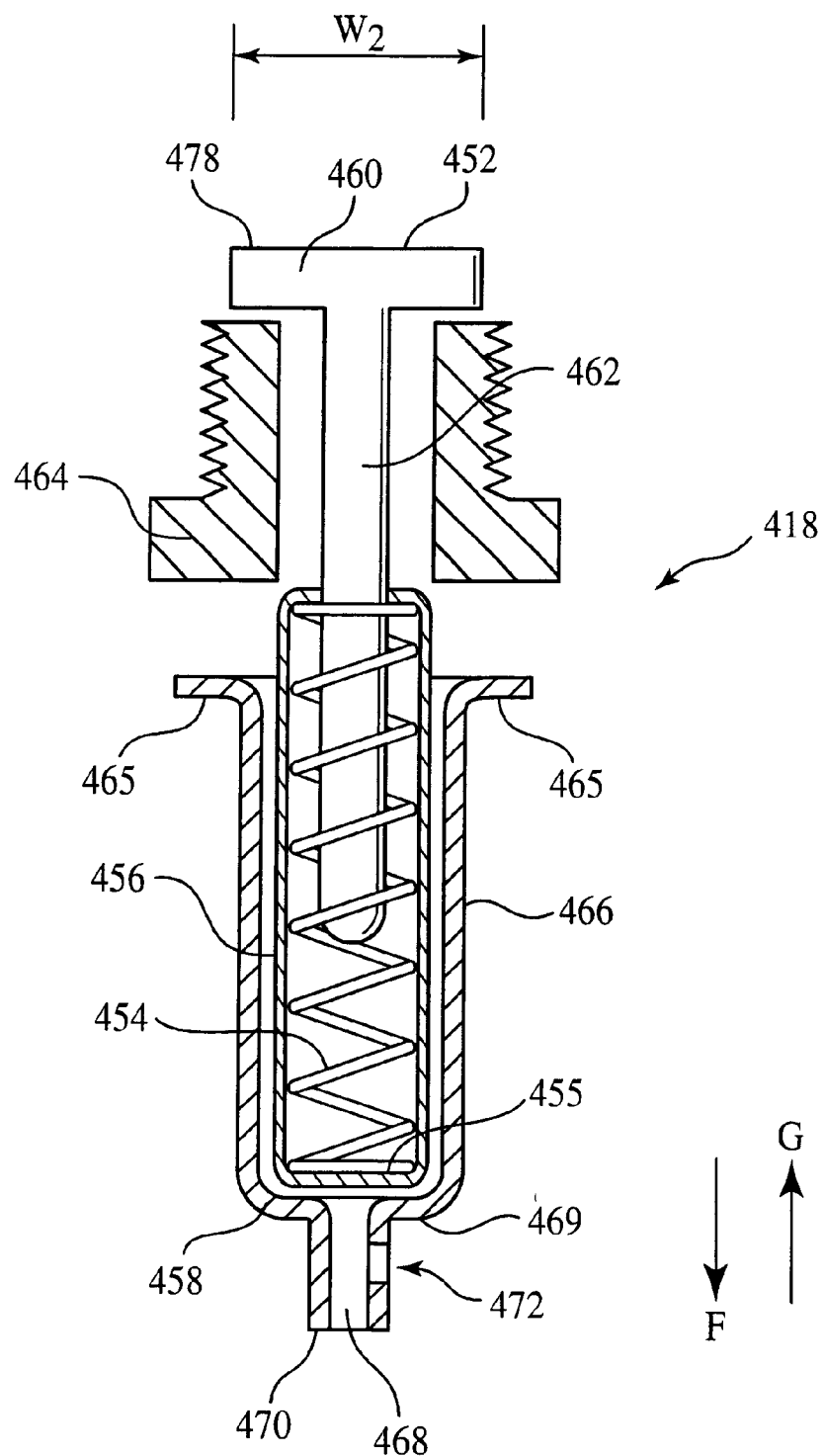
FIG. 8A is an enlarged, sectional view of an alternative, spring mounted fluid transfer stick.

The fluid transfer sticks need not have a flexible sponge tip. Instead, the sticks can include a spring to provide flexibility. Referring to FIG. 8A, a fluid transfer stick 418 includes a pin 452, a spring 454, a spring casing 456, and a metal sleeve 458. Pin 452 includes a transverse head 460, and a shaft 462 that extends into spring casing 456. A head screw 464 rests between head 460 and a shelf 465 of sleeve 458. As described below with reference to FIG. 8C, screw 464 acts to hold stick 418 within its stick holder.

Sleeve 458 includes a generally cylindrical region 466 that surrounds casing 456, and also defines a capillary tube 468 at its tip 470 for transferring a drop of fluid. Capillary tube 468 has a volume of, e.g., about 0.005 ml. When tip 470 is placed in contact with a liquid, capillary action draws about 0.005 ml of the liquid into tube 468. The liquid stays within region 468 until tip 470 is touched against a liquid destination, such as a thin layer chromatography plate. A small hole 472 along the side of capillary tube 468 allows air to escape from region 468, facilitating transfer of liquid.

Spring 454 gives fluid transfer stick 418 flexibility. When tip 470 is pressed against a liquid destination surface, a distal end 455 of casing 456 presses against a proximal end 469 of tube 468, compressing spring 454 within the casing. The spring compresses by, e.g., up to 3.2 mm, allowing movement of sleeve 458 in the direction of arrow G of up to 3.2 mm. When tip 470 is removed from the destination surface, spring 454 decompresses, and sleeve 458 moves in the direction of arrow F until it returns to its extended, biased position.

Figure 8B:
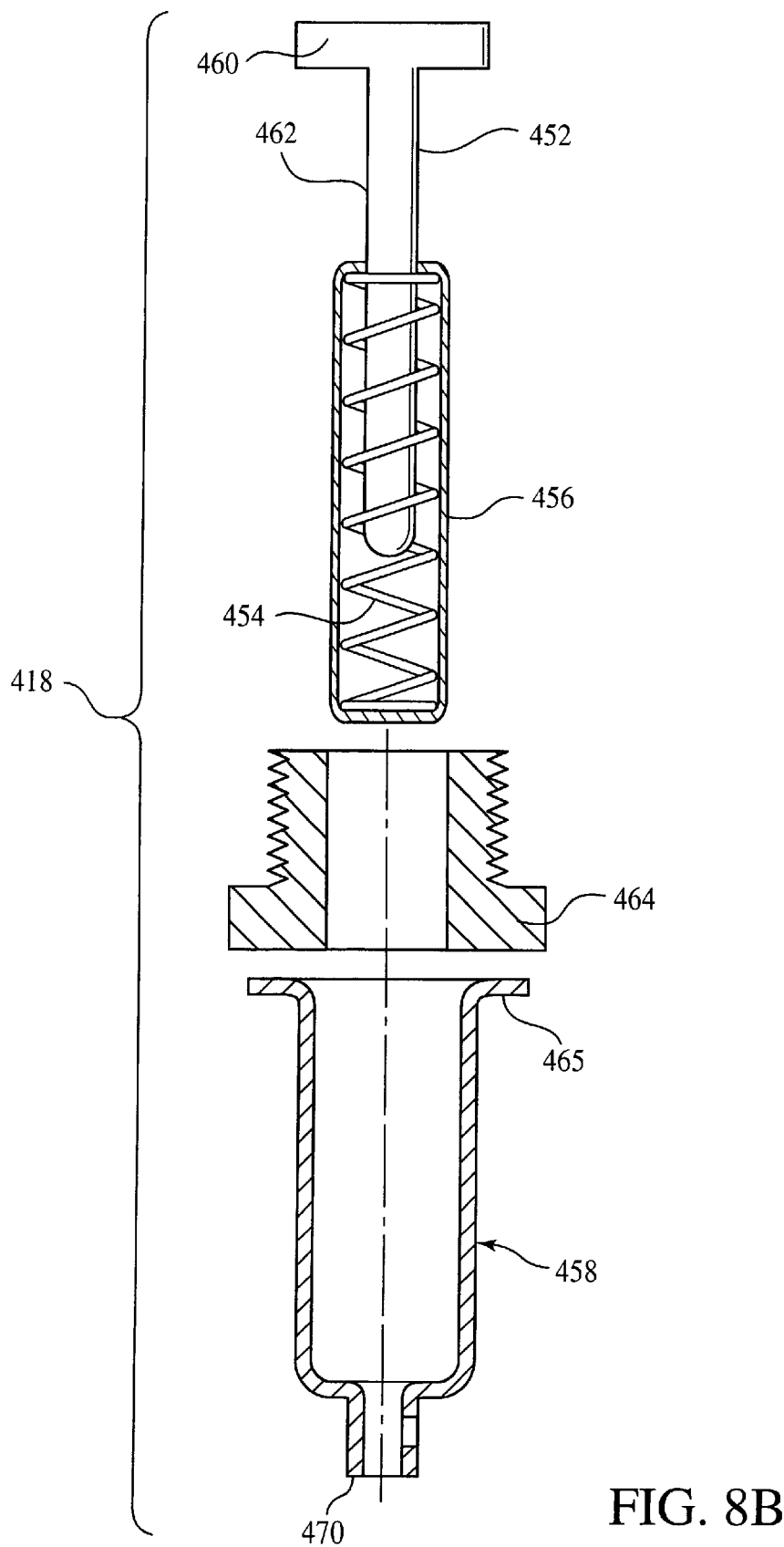
FIG. 8B is an exploded view of the fluid transfer stick of FIG. 8A, illustrating assembly of the stick.

Referring to FIG. 8B, stick 418 is assembled by simply passing casing 456 through head screw 464, into sleeve 458. Casing 456 is maintained within sleeve 458 by a press fit, or by using an adhesive. Pin 452 is pre-assembled within spring 454 and casing 456.

Figure 8C:
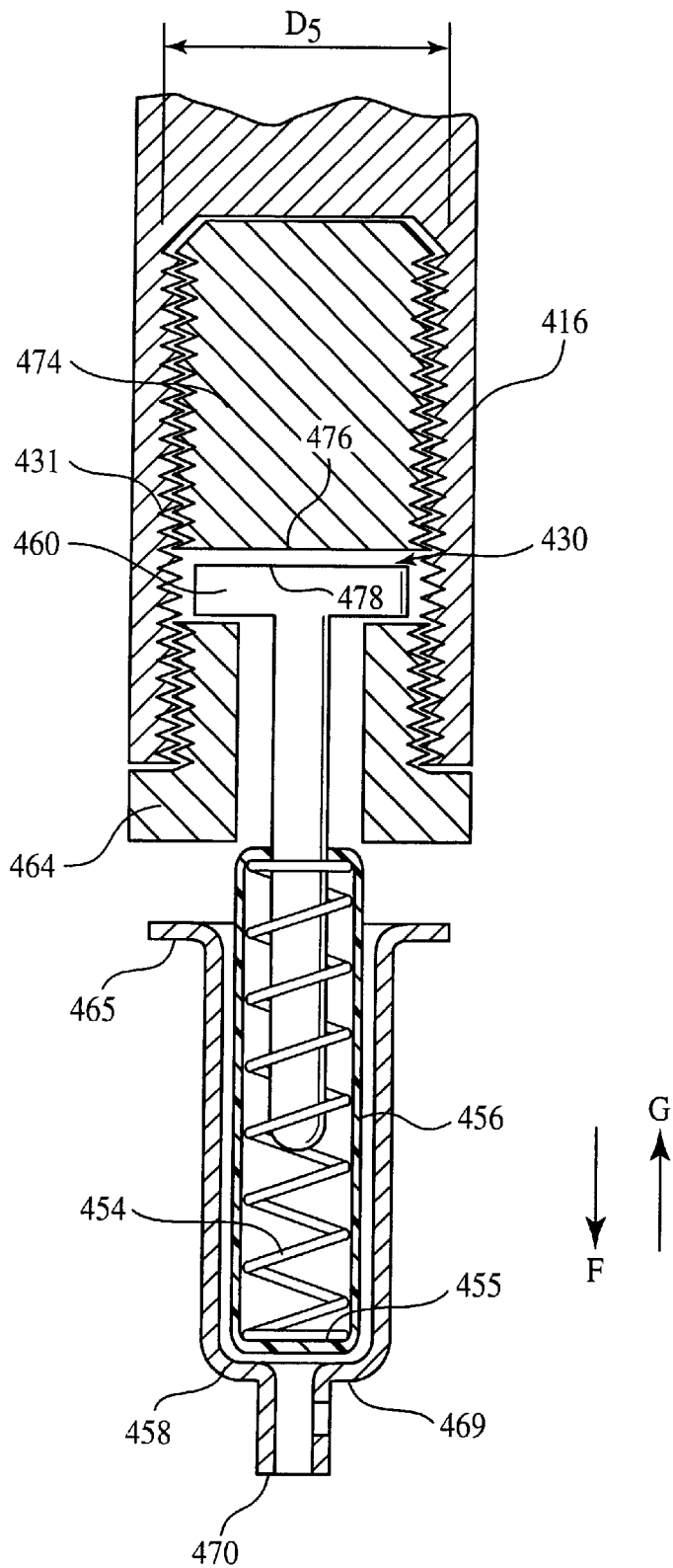
FIG. 8C is an enlarged, sectional view of the fluid transfer stick of FIG. 8A in place within a stick holder.

FIG. 8C illustrates attachment of stick 418 to a stick holder 416. Holder 416 defines an internally threaded bore 430 that has a diameter $D_5$ slightly greater than the width $W_2$ of pin head 460. To hold stick 418 within bore 430, head screw 464 is threadingly engaged with threads 431 of bore 430. An axially adjustable, threaded set screw 474 is also threadingly engaged with threads 431. (The "axial" direction in FIGS. 8A–8C is the direction of arrows F and G.) Set screw 474 is located within bore 430, such that a lower surface 476 of screw 474 rests against, or just above, an upper surface 478 of head 460. Set screw 474 acts to limit movement of pin head 460 in the direction of arrow G.

Holder 416, screws 464 and 474, and pin 452 are made from a metal, such as aluminum, or a rigid plastic. Spring casing 456 is made from a malleable, non-absorbent material, such as nylon. Sleeve 458 is made from a soft metal, such as gold. Unlike sticks 18, the spring mounted tips 418 are not designed to be disposable. Instead, the tips 418 are washed after each use, and can be re-used indefinitely.

A device that has a plurality of sticks 418 and holders 416, rather than holders 16 and sticks 18, is operated in a manner very similar to device 10. In operation, sticks 418 are lowered into, e.g., an array of test tubes, such that tips 470 contact liquid in the test tubes. Each stick 418 draws, by capillary action, about 0.005 ml of liquid into its capillary tube 468. The device is then removed from the test tube array, and the tips 470 are pressed against a liquid destination surface, such as a thin layer chromatography plate. The flexibility afforded sticks 418 by springs 454 ensures that each stick 418 delivers its drop of liquid to the destination surface; if the tips 470 are not perfectly aligned, then the springs 454 of the "longer" sticks compress more than springs of the shorter sticks, such that each stick delivers its liquid drop without breaking.

Variations on the spring mounted sticks 418 and holders 416 are possible. For example, casing 456 can be eliminated. If the casing is eliminated, a proximal end of the spring can be attached directly to the pin shaft or to screw 464, and the distal end of the spring can directly contact proximal end 469 of tube 468. The cylindrical region 466 of sleeve 458 can be shortened, or eliminated altogether. Rather than positioning a head 460 of pin 452 between screws 464 and 474, the pin can be directly attached to the bore of holder 416. For example, the pin can be provided with a threaded region that threadingly engages with the bore. Other modifications of the spring mounted design are possible, and are within the scope of the claims.

The device can have an overall structure different from the structure of device 10. For example, referring to FIGS. 9A–9C, a device 510 has a single support rack 512, rather than upper and lower support racks. Rack 512 has a flat rear surface 580, a curved front surface 582, and rear ledges 484a and 484b. A transverse bar 534 (FIGS. 9B and 9C), similar to bar 134 of FIG. 4B, runs parallel to rear surface 480, from ledge 484a to ledge 484b. Five stick holders 516a–516e are slidably connected to the transverse bar. For example, the bar can pass through transverse holes in each holder, with springs separating the holders, as shown in FIG. 4B. Other mechanisms of slidably connecting the holders to rack 512 can also be used.

Figure 9A:
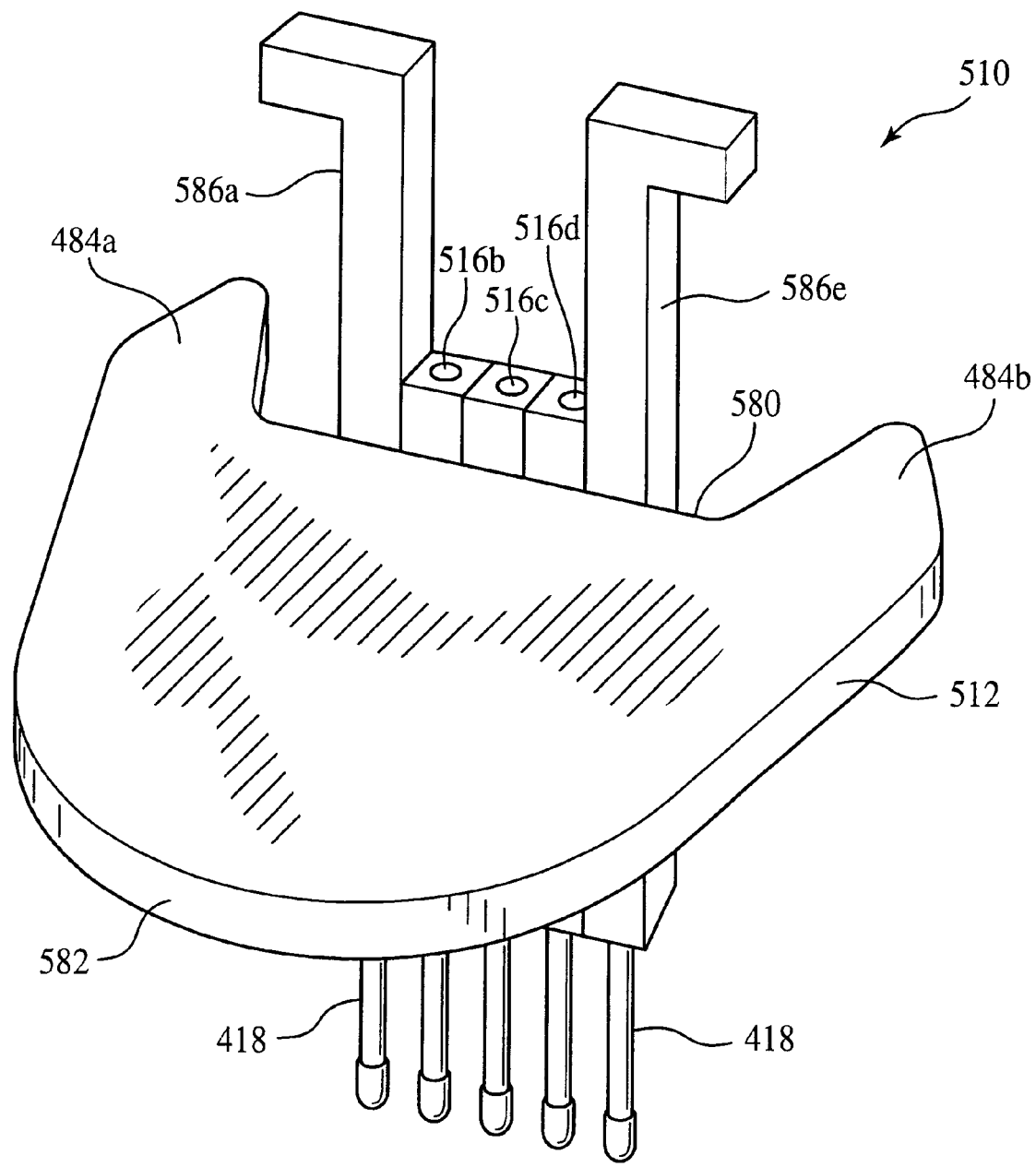
FIG. 9A is a perspective, top view of an alternative fluid transfer device structure.
Figure 9B:
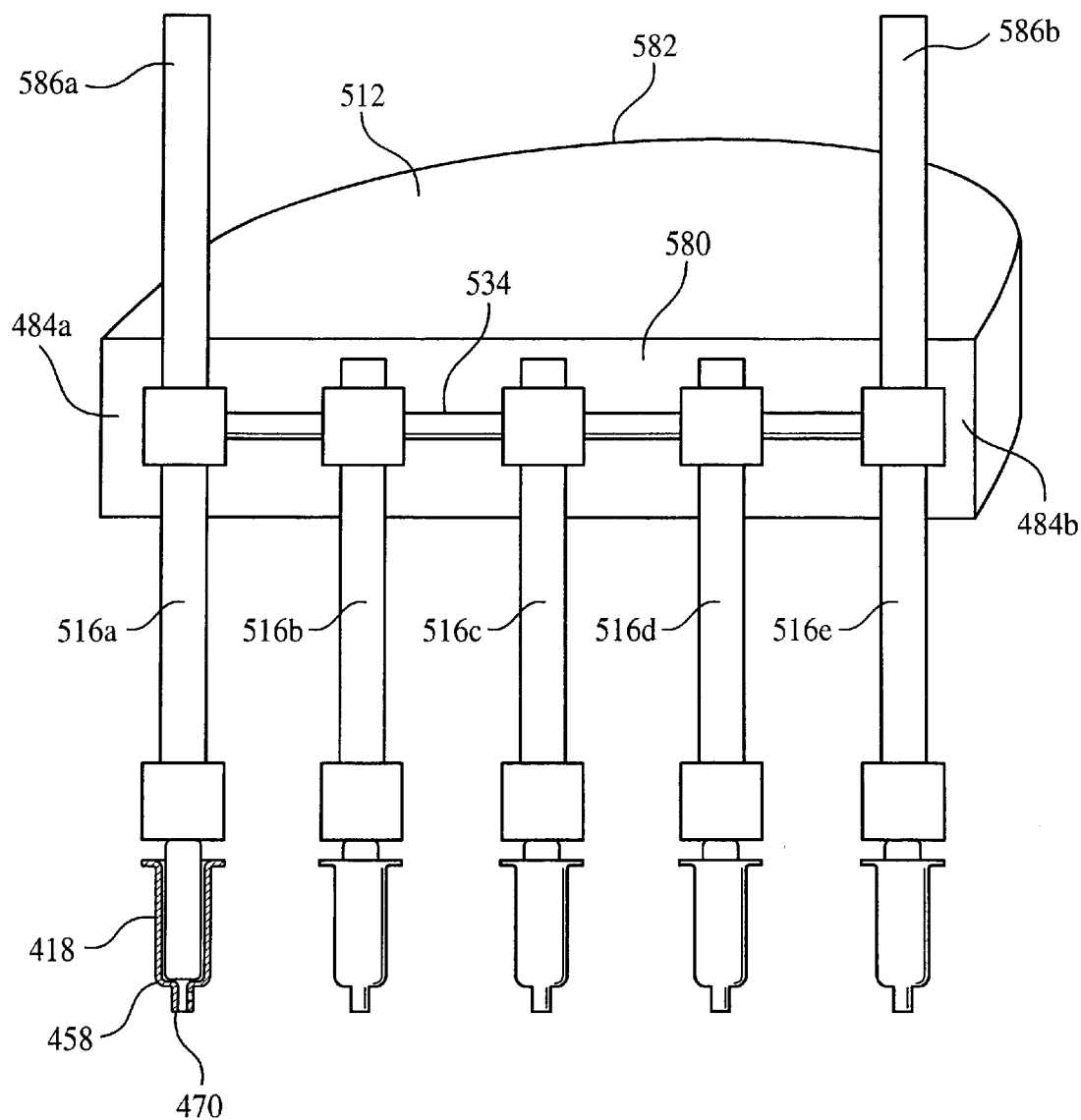
FIG. 9B is a perspective, rear view of the device of FIG. 9A with its stick holders in an expanded position.
Figure 9C:
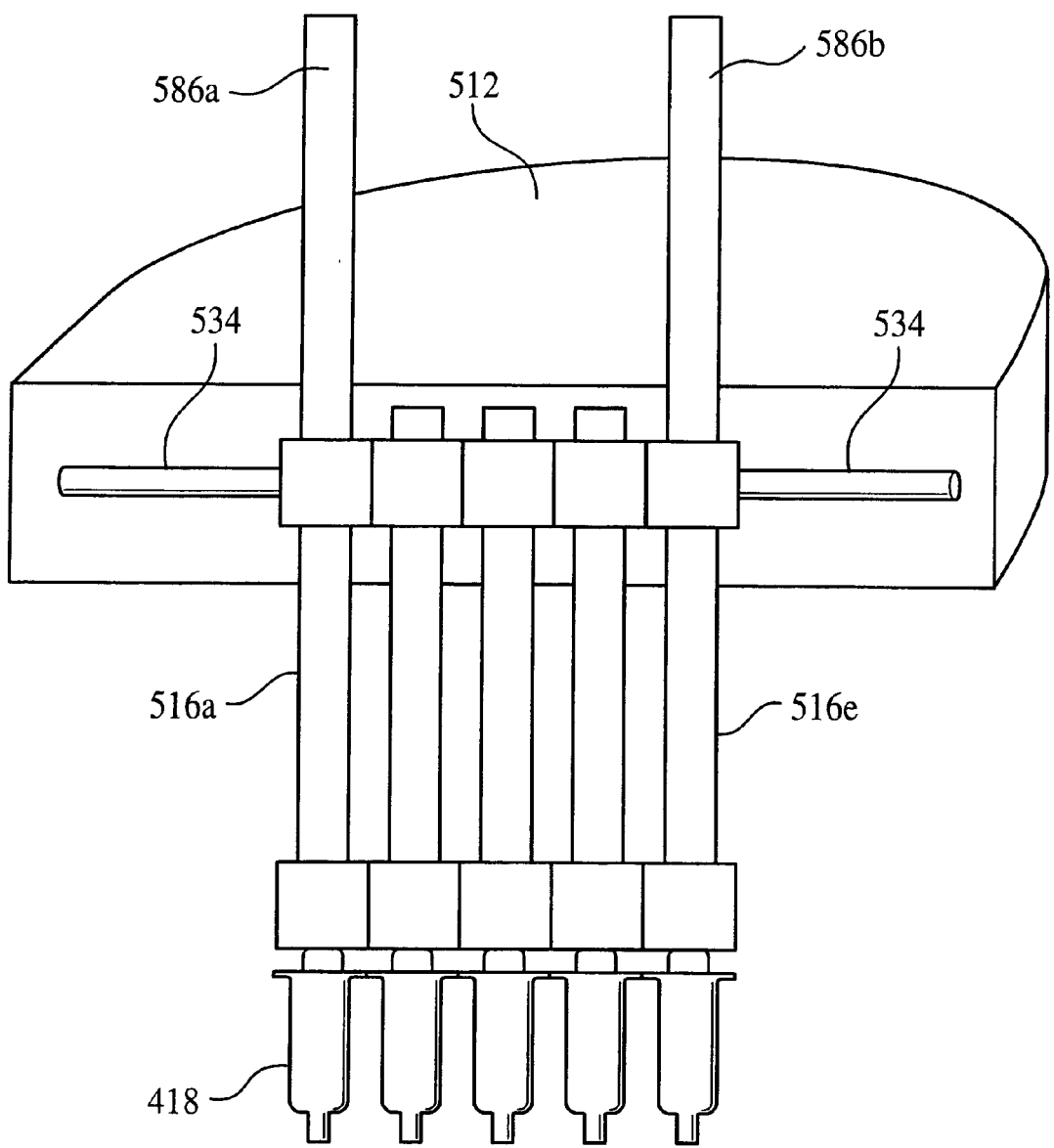
FIG. 9C is a perspective, rear view of the device of FIG. 9A with its stick holders in a contracted position.

Referring to FIGS. 9B and 9C, the five stick holders 516a–516e are slidable from an expanded position (FIG. 9B) to a contracted position (FIG. 9C). The stick holders are biased in their expanded positions by, e.g., springs similar to springs 136a–136d of FIG. 4B.

The two end stick holders, holders 516a and 516e, include axial extensions 586a and 586b. In operation, a user grips device 510 by holding the axial extensions, e.g., between the thumb and index finger of her hand. The user can slide the holders to their contracted positions by simply squeezing axial extensions 586a and 586b towards each other.

The rack and holder structures illustrated in FIGS. 9A–9C can be used with either the spring mounted tips 418, as shown in FIGS. 9A–9C, or with the disposable, sponge tipped sticks 18.

The devices can have different expanded or contracted tip spacings $S_1$ and $S_2$, to accommodate different distances between liquid sources, or different preferred spacing in a liquid destination. In addition, the holders can be biased in their expanded position by structures other than springs. For example, the holders can be separated by a compressible, deformable material, such as a soft rubber.

The number of holders and fluid transfer sticks can be greater or less than five. For example, the device can have only one stick. A simplified device can employ a single flexible stick that is manually dipped into a liquid source by a user, and manually pressed against a liquid destination.

The devices can draw liquid from liquid sources other than test tubes, and can deposit liquid to destinations other than a thin layer chromatography plate. For example, the devices can be used to deposit samples onto an electrophoresis gel. Since the fluid transfer sticks are flexible, the sticks are less likely to damage the gel than rigid pipettes.

What is claimed is:

1. A device for transferring small drops of liquid from one or more liquid holders to one or more liquid destinations, the device comprising:
   a support member; and
   a plurality of fluid transfer members extending from the support member, each fluid transfer member including a flexible liquid transfer end,
   wherein each fluid transfer end comprises a capillary tube at its distal tip, and an axially extending spring, the spring being coupled to the capillary tube such that the spring provides axial flexibility to the tube,
   wherein a distal end of each spring is coupled to a proximal end of each tube,
   wherein each fluid transfer member further comprises a holder for coupling a respective fluid transfer end to the device, and each fluid transfer end further comprises:

a rigid sleeve having a proximal region that surrounds the spring and a distal region that defines the capillary tube; and a pin having a shaft and a head, the shaft extending axially into the spring, and the head being coupled to the holder, wherein each holder defines a threaded bore, and each holder further includes a pair of screws threadingly engaged with the bore, the head of the pin being disposed within the bore between the two screws.

2. A device for transferring small drops of liquid from one or more liquid holders to one or more liquid destinations, the device comprising:

a support member; and a plurality of fluid transfer members extending from the support member, each fluid transfer member including a flexible liquid transfer end, wherein each fluid transfer end comprises a capillary tube at its distal tip, and an axially extending spring, the spring being coupled to the capillary tube such that the spring provides axial flexibility to the tube, wherein a distal end of each spring is coupled to a proximal end of each tube, wherein each fluid transfer member further comprises a holder for coupling a respective fluid transfer end to the device, and each fluid transfer end further comprises:

a rigid sleeve having a proximal region that surrounds the spring and a distal region that defines the capillary tube; and a pin having a shaft and a head, the shaft extending axially into the spring, and the head being coupled to the holder, wherein the capillary tube defines a transverse hole to prevent air from becoming trapped within the tube.

3. A fluid transfer tool for use with a fluid transfer device for transferring small drops of liquid from one or more liquid holders to one or more liquid destinations, the device comprising:

a support member; and a plurality of fluid transfer members extending from the supporting member, each fluid transfer member including a flexible liquid transfer end, the tool comprising:

an axially extending spring having a distal end and a proximal end, and defining an interior;

a capillary tube coupled to the distal end of the spring;

a pin having a shaft and a head, the shaft being disposed within the interior of spring, and the head remaining proximal to the proximal end of the spring; and an attachment member for coupling the tool to the fluid transfer device, the tool further comprising a rigid sleeve, the sleeve having a proximal region that surrounds the spring, and a distal region that defines the capillary tube.

4. The tool of claim 3, wherein the capillary tube defines a transverse hole to prevent air from becoming trapped within the tube.

5. The tool of claim 3, wherein both the proximal and distal regions of the sleeve have a generally cylindrical shape.

6. The tool of claim 3, wherein the attachment member comprises a threaded screw.

* * * * *